US007927251B1

(12) United States Patent  (10) Patent No.: US 7,927,251 B1
Porszasz et al.  (45) Date of Patent: Apr. 19, 2011

(54) EXERCISE TEST SPEED AND GRADE MODIFICATION

(75) Inventors: Janos Porszasz, Lakewood, CA (US); Richard Casaburi, Rancho Palos Verdes, CA (US); Brian J. Whipp, Powys (GB)

(73) Assignee: Los Angeles Biomedical Research Institute at Harbor-UCLA Medical Center, Torrance, CA (US)

( * ) Notice: Subject to any disclaimer, the term of this patent is extended or adjusted under 35 U.S.C. 154(b) by 0 days.

(21) Appl. No.: 12/606,063

(22) Filed: Oct. 26, 2009

Related U.S. Application Data

(63) Continuation of application No. 11/021,372, filed on Dec. 23, 2004, now Pat. No. 7,628,732.

(60) Provisional application No. 60/532,709, filed on Dec. 23, 2003.

(51) Int. Cl.
*A63B 71/00* (2006.01)

(52) U.S. Cl. .................... 482/8; 482/1; 482/51; 482/54; 482/601

(58) Field of Classification Search .................. 482/1–9, 482/51, 54, 900–902; 434/247; 600/300, 600/301; 601/23
See application file for complete search history.

(56) References Cited

U.S. PATENT DOCUMENTS

| 5,018,726 | A |   | 5/1991  | Yorioka  |       |
|-----------|---|---|---------|----------|-------|
| 5,242,339 | A | * | 9/1993  | Thornton | 482/8 |
| 6,174,289 | B1|   | 1/2001  | Binder   |       |
| 6,468,211 | B1|   | 10/2002 | Binder   |       |
| 6,527,674 | B1| * | 3/2003  | Clem     | 482/8 |

OTHER PUBLICATIONS

"Chapter 5 /Clinical Exercise Testing, Section II/Exercise Testing -Exercise Protocols", Jones,N. L. Clinical Exercise Testing, Philadelphia: W.B. Saunders, 1988 (pp. 97-99).
"ATS/ACCP Statement on Cardiopulmonary Exercise Testing", American Thoracic Society/ American Collage of Chest Physicians, American Journal of Respiratory and Critical Care Medicine, vol. 167, 2003 (pp. 211-277).
Euan A. Ashley, et al., "Exercise Testing in Clinical Medicine", Seminar, The Lancet, vol. 356, Nov. 4, 2000 (pp. 1592-1597).
"Handbook of Physiology—Respiration II", Chapter 36: Muscular Exercise (pp. 954-958).
Bruno Balke, M.D., et al., "An Experimental Study of Physical Fitness' of Air Force Personnel", U.S. Armed Forces Medical Journal, vol. X, No. 6, Jun. 1959 (pp. 875-888).

(Continued)

*Primary Examiner* — Glenn Richman
(74) *Attorney, Agent, or Firm* — Blakely Sokoloff Taylor & Zafman LLP (57) ABSTRACT

A treadmill test protocol is provided having a linearly increasing work rate profile achieved by linearly increasing walking speed while simultaneously and non-linearly increasing the treadmill inclination. Specifically, according to the protocol it is possible to use a test subject's projected maximum end-test work rate to calculate a treadmill test protocol that starts with a low walking speed and low grade to produce a metabolic rate that is commensurable to that of unloaded cycling in cycle ergometer tests, thereafter having a linear increase in walking speed and simultaneous curvilinear increase in treadmill grade so that when the test subject is tested according to the calculated protocol, the test result yields a work rate and metabolic rate response with a linear slope. Further, the desired maximum treadmill speed can be adjusted so as there is no need for jogging or running for any given test subject.

21 Claims, 5 Drawing Sheets

OTHER PUBLICATIONS

Ove Bøje, "Energy Production, Pulmonary Ventilation, and Length of Steps in Well-Trained Runners Working on a Treadmill", Laboratory for the Theory of Gymnastics University of Copenhagen, Mar. 31, 1994 (pp. 362-375).

R.A. Bruce, "Exercise Testing of Patients with Coronary Heart Disease Principles and Normal Standards for Evaluation", Annals of Clinical Research, vol. 3, 1971 (pp. 323-332).

Y. Fukuba, et al., "Estimating the Parameters of Aerobic Function During Exercise Using an Exponentially Increasing Work Rate Protocol", Medical & Biological Engineering & Computing, vol. 38, 2000 (pp. 433-437).

Raymond J. Gibbons, M.D., et al., "ACC/AHA Guidelines for Exercise Testing—A Report of the American College of Cardiology/American Heart AssociationTask Force on Practice Guidelines (Committee on Exercise Testing)", JACC, vol. 30, No. 1, Jul. 1997 (pp. 260-315).

James E. Hansen, "Exercise Instruments, Schemes, and Protocols for Evaluating the Dyspneic Patient", American Review of Respiratory Disease, vol. 129, 1984, Supplement (pp. S25-S27).

James E. Hansen, M.D., et al., "Relation ofOxygen Uptake to Work Rate in Normal Men and Men with Circulatory Disorders", American Journal of Cardiology, vol. 59, Mar. 1, 1987 (pp. 669-674).

Edward T. Howley, "The Exercise Testing Laboratory", Chapter 47, Administrative Concerns (pp. 406-413).

A. Huszczuk, et al., "A Respiratory Gas Exchange Simulator for Routine Calibration in Metabolic Studies", Technical Note, Metabolic Calibrator, Eur. Respir. J., 1990 (pp. 465-468).

Jaruki Itoh, M.D., et al., "Oxygen Uptake Abnormalities During Exercise in Coronary Artery Disease", Cardiopulmonary Exercise Testing and Cardiovascular Health, $VO_2$ Kinetics in Coronary Artery Disease, 2002 (pp. 165-172).

Karlman Wasserman, et al., "Exercise Physiology in Health and-Disease", State of the Art, American Review of Respiratory Disease, vol. 112, 1975 (pp. 219-249).

Brian J. Whipp, et al., "A Test to Determine Parameters of Aerobic Function During Exercise", American Physiological Society, 1981 (pp. 217-221).

Brian J. Whipp, et al., "Dynamics of Pulmonary Gas Exchange During Exercise", Chapter 2, Pulmonary Gas Exchange, vol. II, 1980, Academic Press, Inc., ISBN 0-12-744502-1 (pp. 33-96).

Peter M. Will, M.D., "Exercise Testing:Improving Performance with a Ramped Bruce Protocol", American Heart Journal, vol. 138, No. 6, Part 1, Dec. 1999 (pp. 1033-1037).

Roger A. Wolthuis, Ph.D., et al., "New Practical Treadmill Protocol for Clinical Use", Methods, The American Journal of Cardiology, vol. 39, May 4, 1997 (pp. 697-700).

Jerzy A. Zoladz, et al., "Oxygen Uptake Does Not Increase Linearly at High Power Outputs During Incremental Exercise Test in Humans", Accepted: Oct. 30, 1997, Eur. J. Appl. Physiol (1998) 77 (pp. 445-451).

"Bruce and Modified Bruce Treadmill Stress Test Protocols", http://www.leftseat.com/Programs/bruce.htm. 1995.

"Conditioning for the FAA Treadmill Stress Test", http://www.leftseat.com/tmst.htm, 1995.

* cited by examiner

EXERCISE TEST SPEED AND GRADE MODIFICATION

CROSS-REFERENCE TO RELATED APPLICATION

This application is a continuation of U.S. patent application Ser. No. 11/021,372 filed Dec. 23, 2004, which claims the benefit of the earlier filing date of co-pending U.S. Patent Application No. 60/532,709, filed Dec. 23, 2003, and incorporated herein by reference.

FIELD

Exercise equipment speed and grade protocol determination.

BACKGROUND

To assess the health of the cardiovascular and pulmonary systems of a subject, a subject is often tested on a piece of exercise equipment to the subject's limit of tolerance or point of exhaustion while measurements of metabolism are taken. For example, during a cardiovascular initial assessment exercise test for exercise intolerance, it is often desirable to exercise a test subject on exercise equipment according to a test protocol that increases the testing subject's work rate and, consequently, the subject's oxygen uptake utilization over time. Specifically, treadmill exercise tests that gradually expand the tolerable work rate range of the test subject during the test may be used to provide an initial assessment of the subject. However, current treadmill protocol tend to miss the mark of providing a work rate and oxygen uptake response that begins low enough for severely limited subjects, and increases steadily and quickly enough to exhaust the subject within an appropriate time period.

SUMMARY

In one embodiment, a method is described. One method includes determining treadmill test control data to cause a change in treadmill speed with respect to time and a simultaneous change in a treadmill angle of inclination with respect to time, wherein, both the change in the treadmill speed and the angle of inclination are determined prior to beginning a treadmill test and in accordance with characteristics of the subject known before the test. More specifically, according to one example, a treadmill exercise test protocol requiring a low initial metabolic rate may be incremented linearly to reach the subject's limit of tolerance (e.g., such as at the point of exhaustion when the subject is unable to continue exercising on the treadmill). Using such a protocol, it is possible to set a predetermined time for the test, such as 10 minutes, and to allow for exercise testing and rehabilitation of either normal subjects or subjects with impaired exercise tolerance for a period of time that is approximately equal to that predetermined time. One such treadmill protocol includes a linear increase in walking speed coupled with a simultaneous curvilinear increase in treadmill grade to yield a linear increase in work rate. Moreover, this combination of simultaneous increase in speed and grade can be calculated for test subjects having a wide variety of various projected maximum end-test work rates, so that when a test subject is tested according to the protocol, the test result yields a linear work rate slope that allows the linear oxygen uptake response to be appropriately interpreted.

BRIEF DESCRIPTION OF THE DRAWINGS

Various features, aspects, and advantages will become thoroughly apparent from the following detailed descriptions, the set of claims, and accompanying drawings in which:

DETAILED DESCRIPTION

An incremental exercise test, that linearly spans the tolerable work rate range, is widely recommended as a procedure for initial assessment in clinical exercise testing. In these tests, work rate may be advanced either as a ramp function (e.g., continuous increase) or using frequent stepwise increases in work rate. These tests are normally performed using either a cycle or treadmill ergometer. However, it is possible that the treadmill may induce a higher maximum metabolic rate and may use a mode of exercise that more closely approximates aspects of activities of daily living. Since the linearity of the pattern of the oxygen uptake response is a major discriminating feature for assessing a cardiovascular basis for exercise intolerance, it is naturally important to be confident of the linearity of the work rate profile that yielded the response.

For severely impaired patients, the metabolic cost of even normal walking or unloaded cycling can be a significant proportion of their maximum metabolic rate, which in turn limits the duration of the test and, consequently, the available range of data for interpretation. However, an incremental treadmill test starting at a slow and constant walking speed could provide a sufficiently low initial metabolic rate, but keeping the speed constant as the test progresses may result in an inappropriately long test duration. Conversely, a faster and constant walking speed, while shortening the test, has the disadvantage of a high initial metabolic cost. Consequently, a combination of an initially slow walking speed that is increased progressively in concert with an increasing grade may meet the demands of both an initially low exercise metabolic rate and optimum test duration.

Thus, according to one embodiment, a treadmill exercise test is designed and implemented that: a) requires a low initial metabolic demand; b) provides a constant rate of change in work rate (i.e., linear increase as a function of time) utilizing simultaneous changes in both speed and grade; and c) brings subjects to the limit of tolerance within a selected time (e.g., in approximately 10 minutes, i.e., meeting the requirements currently recommended for clinical exercise testing by relevant major international organizations). As a result, this protocol may be performed with subjects with severely limited exercise tolerance (e.g., those with severe heart or lung disease), as well as healthy subjects with widely differing exercise tolerances. For example, the treadmill protocol cardiopulmonary and metabolic response profiles of healthy sedentary individuals and patients with limited exercise tolerance using according to this embodiment of a treadmill protocol may be compared with those from a cycle ramp test with an equivalent work rate incrementation profile.

Protocol Design

The rate of work done against gravity while walking up an incline generally depends on a subject's weight, the walking speed and the angle of inclination itself. Specifically, with respect to time (t):

$$WR(t) = m \cdot g \cdot v(t) \cdot \sin(\alpha) \tag{a}$$

where WR(t) is the time course of work rate in Watts,

'm' is body mass in kilograms (kg),

'g' is the gravitational acceleration in meters per square second ($m/s^2$) (9.81 $m/sec^2$), 'v(t)' is the time course of velocity in meters per second (m/s) (m/sec), and 'α' is the angle of inclination.

Figure 1:
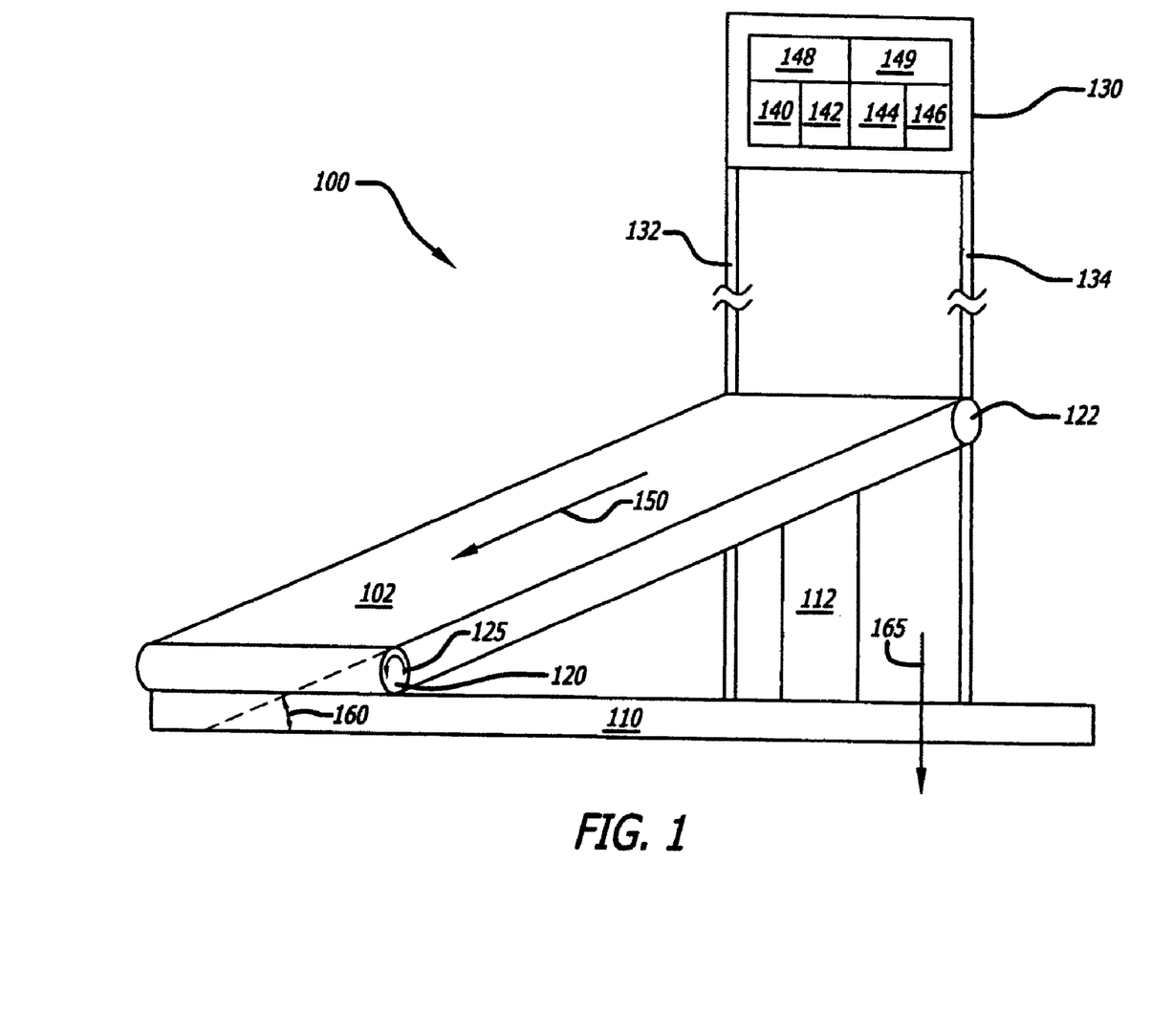
FIG. 1 is a schematic side prospective view of an exercise treadmill.

In terms of a treadmill system, although the expressions 'inclination', 'angle' and 'grade' all refer to the slope of the treadmill belt, the terms are not synonymous. Inclination and grade refer to the "rise/run" of the treadmill. Inclination and grade are therefore related to and may be equal to the tangent of the angle of inclination (e.g., angle 160), and expressed as percentage (i.e., units of rise per 100 units of run). Also note that for purposes of a treadmill system generally, the work rate equation considers only that work done against gravity (i.e., calculated work rate will be zero, when the grade is zero).

Two ways to achieve a linear increase in work rate are: 1) to maintain a constant inclination while increasing the speed linearly and 2) to maintain a constant speed while increasing the sine of the angle of inclination linearly (e.g., such as by increasing the angle of inclination linearly). However, with the first option, a choice of a low inclination means that for a reasonable duration (such as 10 minutes), the speed may be increased to such a fast pace that tolerance may be dictated by the ability to move the legs quickly and/or efficiently enough rather than metabolic factors. Alternatively, the choice of a steeper grade may yield a high initial metabolic cost. With the second option, the choice of a low speed means that treadmill inclination may increase to a very steep grade before tolerance is reached, whereas the choice of a higher initial speed may yield a high initial metabolic cost.

Consequently, in one embodiment a treadmill protocol is described that features a linear increase in work rate that starts with a slow speed, which is advanced linearly such that a subject fatigues at a moderate walking speed due to metabolic, cardiac and/or pulmonary reasons other than being unable to walk fast enough due to mechanical reasons. To accomplish this, the treadmill slope may be incremented in a pattern predetermined to yield a linear work rate profile with respect to time (t). Thus, if:

$$WR(t) = S \cdot t + WR_0 \tag{b}$$

where S is the work rate slope (watts/min) and $WR_0$ is the initial work rate, and $$V(t) = V_s \cdot t + V_0 \tag{c}$$

where $V_s$ is the rate of change of velocity ($m/sec^2$) and $V_0$ is initial treadmill velocity, then $$S \cdot t + WR_0 = m \cdot g \cdot (V_s \cdot t + V_0) f(t) \tag{d}$$

where f(t) is the time course of sin(α).

Rearranging:

$$f(t) = S \cdot t + WR_0 / m \cdot g \cdot (V_s \cdot t + V_0) \tag{e}$$

Certain considerations may lead to a highly useful computational form of this equation. First, the incremental phase of the exercise test can be for a reasonable duration, such as between 6 minutes and 25 minutes. Specifically, the work rate slope (S)(t) may be designed or prescribed so that the limit of tolerance is reached in approximately 10 minutes. Therefore:

$$S = (WR_{max} - WR_0)/10 \tag{f}$$

where $WR_{max}$ is the projected or predicted maximum end-test work rate.

Second, if the desired end exercise treadmill velocity is specified as $V_{max}$, then:

$$V_s = (V_{max} - V_0)/10 \tag{g}$$

Finally, for most treadmills, the slope of the treadmill can be programmed as the grade, which is the tangent of the angle of inclination. Therefore:

$$f(t) = \sin(\arctan(\text{grade})) \tag{h}$$

By trigonometric identity:

$$f(t) = \text{grade}/\text{SQRT}(1+\text{grade}^2) \tag{i}$$

According to embodiments, for the range of treadmill grades typically encountered during exercise testing, the denominator of this equation is very near 1, so that f(t) and the grade are very nearly equal (e.g., for a grade of 0.05 (a 5% grade), f(t) is 0.499; for a grade of 0.20, f(t) is 0.196).

Thus, one example embodiment of a 10 minute time course of the inclination, grade (t), predicted to achieve a linear increase in work rate is:

$$\text{grade}(t) = \{[(WR_{max}/m \cdot g \cdot V_0) - \text{grade}_0] \cdot t + 10 \cdot \text{grade}_0\}/\{[(V_{max}/V_0) - 1] \cdot t + 10\} \tag{j}$$

Therefore, the time course of inclination, grade (t), can be calculated based on a subject's body weight, the desired initial and final treadmill speeds ($V_0$ and $V_{max}$), the initial grade ($\text{grade}_0$) and the predicted peak work rate. While this procedure provides a pure smooth linear ramp of work rate, with appropriate electronic control of the treadmill's incremental ability to increase speed and grade, its functional equivalent for testing a subject can also be generated. For example, small increments of work rate expressed over time intervals that are short relative to the response kinetics of the variables of interest of equation (j) can be used to yield a response that is indistinguishable from that of a "pure" ramp (e.g., indistinguishable from that of a pure smooth linear ramp).

FIG. 1 is a schematic side prospective view of an exercise treadmill. FIG. 1 shows treadmill 100 having belt 102, base 110, support 112, and console 130. Belt 102 is connected to, (e.g., wrapped around) roller 122, and actuator 120. In one embodiment, console 130 may be attached to one or more other structures mentioned above such as by being attached to base 110 via coupling 132 and coupling 134.

Moreover, an embodiment can be implemented as computer software in the form of computer readable code to be executed on a microprocessor. For example, console 130 may include processor 140 coupled to memory 142, controller 144, media reader 146, data input 148, and display 149. Thus, in one embodiment, processor 140 may be a microprocessor, including a dedicated uniquely designed architecture processor, or any other suitable microprocessor or microcomputer. Thus, processor 140 can be a processor sufficient to execute computer software embodied in a computer program product. Similarly, in embodiments, memory 142 may be a memory sufficient to store the necessary data and/or software for execution and/or manipulation by processor 140 (e.g., memory 142 may be random access memory (RAM) and/or read only memory (ROM)).

In addition, embodiments include computer software embodied in any form of computer program product. A computer program product may be a medium configured to store or transport computer readable code, or a medium in which computer readable code may be embedded. Some examples of computer program products are CD-ROM-disks, ROM cards, floppy disks, magnetic tapes, computer hard drive, and flash-memory.

Further, in accordance with embodiments, media reader 146 may be a reader sufficient to read electronic data from magnetic or optical disks, cards, wireless signals, etc. Similarly, data input 148 may be an input sufficient to input data such as a keyboard, touch screen, voice recognition device, telephone link, electronic network link, etc. Furthermore, display 149 may be a display sufficient to display information related to the treadmill, protocol, and/or treadmill test, such as a cathode ray tube (CRT), liquid crystal display (LCD), or thin-film transistor (TFT).

Likewise, controller 144 may be a controller sufficient to provide one or two-way communication (e.g., such as control data and/or control signals such as voltages for causing an actuator or motor to move) between console 130, support 112, and actuator 120. For example, controller 144 may provide control data or signals to, and receive control data or signal feedback from, support 112 and actuator 120 (e.g., such as by sending data and/or signals via wires, wireless communication, data buses, fiber optics, and/or a data cables).

Consequently, according to embodiments, during a treadmill exercise test of a test subject, belt 102, actuator 120, roller 122, support 112, and/or base 110 are capable of adjusting speed 150 over a range of speeds and angle of inclination 160 over a range or grades. Thus, embodiments have the necessary hardware and software functionality for adjusting speed 150 of belt 102 via actuator 120 and/or adjusting a height of support 112 so as to control angle of inclination 160 of the treadmill belt top from a horizontal plane corresponding to the plane on which base 110 rests. Specifically, actuator 120 may be a motor or other appropriate device for imparting a rotation to belt 102 to effect movement of belt 102 in a direction similar to that shown by direction arrow 125, such as to cause a change in or maintain a speed of treadmill speed 150. In addition, in embodiments, actuator 120 may have the capability to effect a movement of belt 102 in a direction opposite the direction shown by direction arrow 125. Also, movement of belt 102 may be effected by various other appropriate actuation means such as by including an actuator at roller 122 as well as at actuator 120, by switching the location of actuator 120 with roller 122 and/or by various other appropriate mechanisms. In embodiments, angle of inclination 160 is an angle between a plane normal to the vector of gravitational pull 165 at the location of treadmill 100 (e.g., such as shown by base 110) and the angle of inclination of a plane containing the top surface of belt 102.

For instance, according to embodiments, angle of inclination 160 may be adjusted by raising the end of belt 102 (e.g., the end of the treadmill walking surface) proximate to roller 122, by lowering the end of belt 102 proximate to actuator 120, or by both raising and lowering those ends to tilt the walking surface of belt 102 along an axis parallel to the axis of roller 122 and/or actuator 120. Note, that it is contemplated that belt 102 include a platform within belt 102 to accept the weight of a subject using treadmill 100, such as by transferring the weight of the subject to support 112.

As a result, a machine readable medium having data therein, such as data in memory 142 and/or a medium read by reader 146, may be accessed by processor 140 to cause a computer, such as console 130 to pre-determine treadmill test control data (e.g., such as by determining the test control data prior to beginning a treadmill test), that will cause a change in treadmill speed with respect to time, and an associated change in treadmill angle of inclination with respect to time; according to treadmill test initial conditions.

For example, in accordance with embodiments, processor 140, memory 142, input 148 and/or media reader 146 may contain or access electronic code which when executed obtains treadmill test information and determines treadmill test control data. More particularly, treadmill test information (e.g., such as treadmill test initial conditions) may be input, obtained, determined and/or provided to processor 140 via data input 148, media reader 146, and/or memory 142 in order to obtain one or more of a total test time for a treadmill test, a test subject's weight, height, age, gender, and/or fitness level. The treadmill test information may include a predicted peak work rate for a test subject, such as described below with respect to FIG. 2 and may be stored in memory 142.

After obtaining treadmill test information it is possible for treadmill test control data associated with the test information to be determined, prior to beginning a treadmill test, such as by calculations performed by processor 140 using data in memory 142. Furthermore, test control data may be stored in memory 142 written to writeable media via media reader 146 or output to another electronic device such as an electronic output or communication device.

Also, according to embodiments, test control data may include treadmill speed control data to cause an increase in treadmill speed 150 with respect to time and corresponding treadmill angle of inclination control data to cause a non linear increase in treadmill angle of inclination 160 with respect to time that is inversely related to the increase of speed 150 over time. Specifically, controller 144 may use such test control data to increase treadmill speed 150 with respect to time via actuator 120, as described above; and to cause a simultaneous corresponding non linear increase in treadmill angle 160 such as via raising and lowering a height of support 112 coupled to belt 102, as described above.

Figure 2:
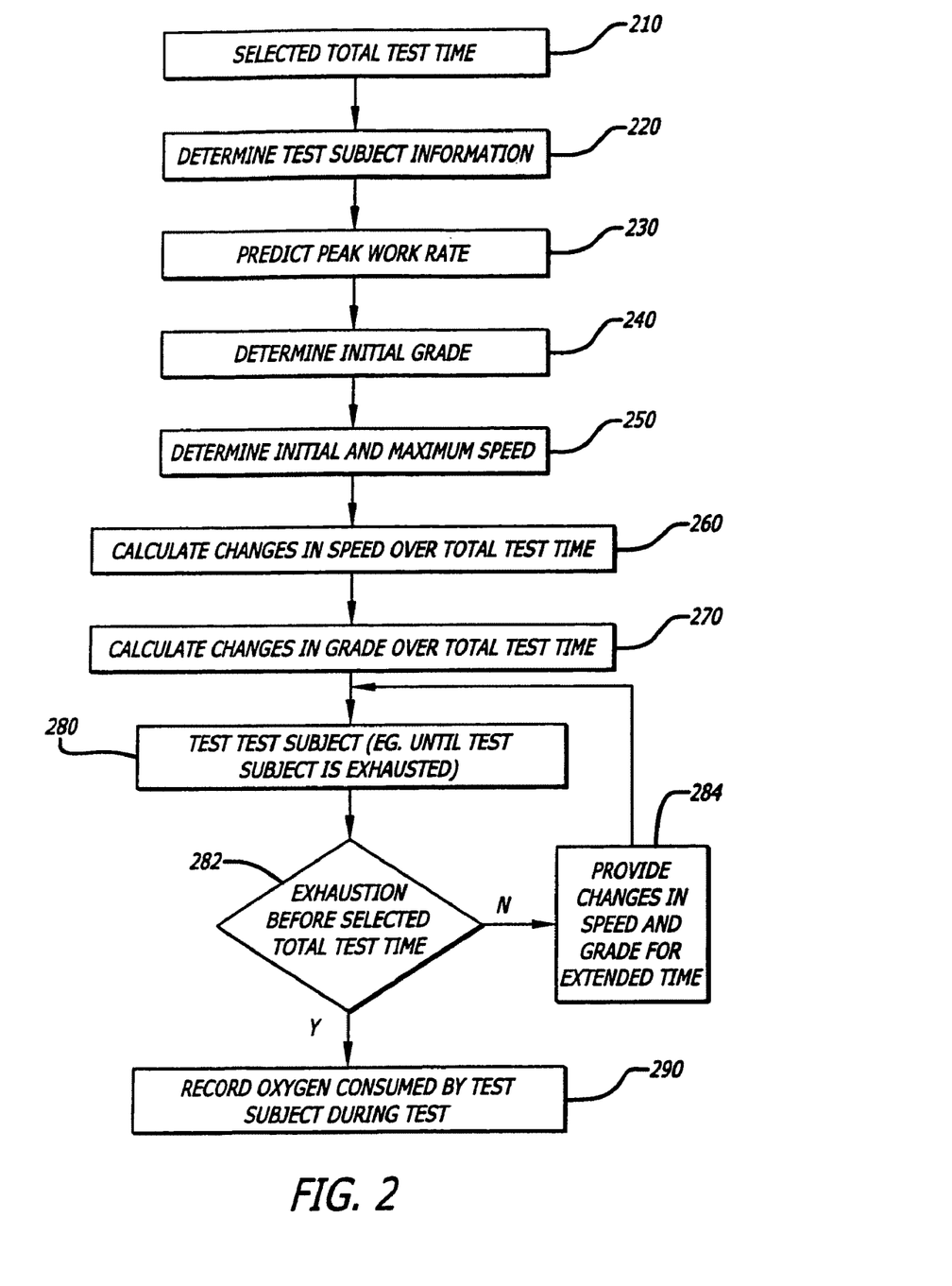
FIG. 2 is a flow diagram of a process for determining treadmill test speed and grade changes.

For instance, FIG. 2 is a flow diagram of a process for determining treadmill test speed and grade changes. At block 210 a total test time is selected. For example, a test initialization period, test duration period, and/or test extended time period may be selected depending on the treadmill test to be administered, (e.g., such as by selecting a three minute initialization period, a 10 minute test duration period, and a five minute test extended period for a treadmill cardio test according to a protocol as described herein). Note that the test duration period described above may correspond to a "total test time" as used and described herein. Also, a "total test time" may equal a test initialization period, a test duration period, and a test extended period (e.g., such as a test extended period as will be described further below for block 284).

At block 220 test subject information is obtained, input, or determined such as via data input 148, media reader 146, and/or memory 142 as described above with respect to FIG. 1. For example test subject information may include one or more of a test subject's weight, height, age, gender, fitness level, predicted peak work rate, initial angle of inclination, initial treadmill speed, maximum total test duration time, and maximum treadmill speed for a test to be administered to the test subject. Likewise, in embodiments, test subject information may include a total test time, a test initialization period, test duration period, and/or a test extended time.

At block 230, a peak work rate for the test subject is predicted or determined (e.g., such as a projected or predicted maximum end-test work rate as mentioned above). For example, according to embodiments, the peak work rate may be entered or obtained similarly to obtaining test subject information as described above with respect to block 220. In addition, in embodiments, the peak work rate may be predicted based on one or more of a test subject's weight, height, age, gender, and fitness level (e.g., such as by looking up a predicted peak work rate in a table considering one or more of those characteristics).

For instance, in one embodiment, at block 230, the predicted peak work rate is obtained such as from a published table or formula. Moreover in some embodiments, the predictor peak work rate may be modified by an estimate of the patient's level of disability prior to initiating a treadmill test. For instance, peak work rate may be a value input at data input 148, and may be modified, such as by a test administrator inputting predicted peak work rate modification data at data input 148, such as to manipulate the value of the inputted predicted peak work rate value up or down and amount associated with the predicted peak work rate modification data. Further, note that in some uses, the maximum work rate attained on the treadmill during a test according to protocol described herein, may differ slightly from those projected or predicted by a formula or table, and in some uses there may be marked variability (i.e., the actual tested value averaging 105 percent of that predicted by the formula, but with a large standard deviation of for instance 25 percent). Therefore, it is possible to set or select the peak work rate at a somewhat higher value than that predicted by a published table or formula (e.g., such as approximately 30 percent higher) in order to ensure that subjects who have a higher exercise tolerance than that of the predicted title or formula mean are also accommodated by the protocol test. Thereby, for example, if the test exceeds a maximum total test duration, such as a 10-minute target, the subject's actual test work rate could, still increase effectively linearly. This is because according to embodiments, the test protocol grade continues to increase slowly as it approaches its asymptotic value and the test protocol treadmill speed, continues to increase linearly, allowing the linearity of the work rate to be sustained. In these cases the predetermined maximum speed can also (and must) be exceeded such that the linearity of the work rate to be sustained beyond the predetermined 'target' maximum speed. For example, the predetermined maximum speed may be modified such as is described above with respect to modifying the predicted work rate at block 230.

At block 240, an initial grade is determined for a treadmill test according to a protocol as described herein. For example, in embodiments, an initial grade may be selected from the potential grades available according to the capability of the treadmill the test is going to be administered using. Moreover, an initial grade may be input or obtained such as similarly to obtaining test subject information as described above with respect to block 220. Also note that for most treadmills, the slope of the treadmill or angle of inclination 160 is programmed as the grade, which is actually the tangent of the angle of inclination because for the range of grade commonly encountered in treadmill exercise testing, the slope or angle of inclination is approximately equal to the grade (e.g., such as is described further above and as will be described further below with respect to FIGS. 3A-3D).

Moreover, at block 240, according to embodiments, in addition to determining initial grade, a maximum possible grade may also be determined, obtained, or input, such as a maximum possible grade available in accordance with the capability of the treadmill on which the test is to be administered. For instance, a maximum possible grade may be obtained or determined such as described above with respect to obtaining test subject information at block 220.

At block 250 an initial speed is determined for a treadmill test according to a protocol as described herein. For example, an initial speed may be selected from speeds available within the capability of the treadmill on which the test is to be administered. Furthermore, an initial speed may be input or obtained, such as is described above with respect to obtaining test subject information at block 220.

Likewise, at block 250, according to embodiments, in addition to determining initial speed, a maximum possible speed may also be determined, obtained, or input, such as a maximum desired speed available in accordance with the capability of the treadmill on which the test is to be administered. Furthermore, a maximum possible speed may be obtained or determined such as is described above with respect to obtaining test subject information at block 220.

Thus, at block 250, a treadmill speed range may be determined. For instance it may be useful in some cases to keep the initial speed slow (e.g., 0.5 mph i.e. 0.25 m/sec, or the lowest value achievable (e.g., 1.0 mph with "older" treadmills) to assure providing a low initial metabolic rate (e.g., see initial test speed 334 of FIGS. 3A-3D). In embodiments, the top speed can be chosen according to the subject's ability to walk comfortably (e.g., which, for a debilitated subject, might be as low as 1-1.5 mph, and for a healthy subject might be up to 3.5-4.0 mph).

At block 260, changes in treadmill speed over the total test time are calculated for a treadmill test. For example, according to embodiments, a non-zero change in treadmill speed with respect to time, (e.g., such as a linearly increasing treadmill speed with respect to time) may be calculated prior to administering the test (e.g., such as described with respect to FIGS. 3A-3D and 4A-4D). Specifically, according to embodiments, changes in treadmill speed over time may be calculated prior to a treadmill test, such as according to equation (c) and (g) as described herein, so as to correspond to simultaneous changes in angle of inclination as calculated according to equation (j) or (k) as described herein. Thus, prior to beginning a treadmill test, changes in treadmill speed with respect to time may be predetermined by calculations made by processor 140 and/or controller 144, and/or including data stored in memory 142.

Consequently, for instance, a treadmill test protocol may use a linear increase in belt speed which can be adjusted to be within the subject's comfortable walking range, usually from about 0.5 mph up to a maximum of about 3.0 mph, although both the initial speed and the projected maximum can be adjusted according to the subject's ability to walk. However, in order to achieve the linear increase in work rate it is possible to increment the treadmill inclination in a curvilinear fashion.

For instance, at block 270, changes in treadmill grade over the total test time are calculated for a treadmill test, such as by calculating treadmill angle of inclination control data to cause a change in treadmill angle of inclination over time, prior to administering the test. For example, a non-linear or inverse exponential angle of inclination with respect to time may be calculated to cause a change in treadmill angle of inclination with respect to time for a treadmill test protocol as described herein (e.g., such as is described with respect to FIGS. 3A-3D and 4A-4D). Moreover, according to embodiments, changes in treadmill grade over time may be calculated according to equation (j) or (k) as described herein, such as by performing calculations at processor 140, controller 144, and/or using data stored in memory 142. Likewise, changes in treadmill angle of inclination over time may be calculated similarly to as described above with respect to changes in treadmill grade over time, wherein the change in treadmill angle of inclination asymptotically approaches a maximum angle of inclination, defines a function drive by calculating a change with respect to time according to $[(WR_{max}/m \cdot g \cdot V_0)-\text{grade}_0]$, and $1/[(V_{max}/V_0)-1]$, wherein, $WR_{max}$ is the predicted peak work rate, 'm' is a body mass in kg for the test subject, 'g' is gravitational acceleration (9.81 m/sec$^2$), $V_0$ is an initial treadmill speed, $V_{max}$ is a maximum treadmill speed, and $\text{grade}_0$ is an initial angle of inclination of the treadmill.

It is also contemplated that changes in treadmill speed and/or grade with respect to time may be recalculated. For example, if a test administrator is dissatisfied with the treadmill speed, changes in treadmill speed, treadmill angle of inclination, changes in treadmill angle of inclination, treadmill grade, changes in treadmill grade, treadmill work rate, and/or changes in treadmill work rate with respect to time for changes in treadmill speed and/or changes in treadmill grade calculated with respect to time, the test administrator may calculate a subsequent set of changes in treadmill speed and/or changes in treadmill grade with respect to time. Specifically, the treadmill administrator may perform a subsequent calculation of changes in treadmill speed with respect to time and changes in treadmill grade with respect to time as described above for blocks 160 and 270.

Specifically, changes in speed may be calculated at block 260 and changes in grade may be calculated at block 270 dependent on a test subject's predicted peak work rate, such as described above with respect to block 230, and a maximum total test duration time or total test time as described above with respect to block 210. Moreover, in embodiments, calculations for block 260 and block 270 may also consider the information described above with respect to blocks 210, 220, 230, 240, and 250.

Furthermore, according to embodiments, the total test time (e.g., such as total test time described with respect to block 210) may be divided into a plurality of test time increments and the changes in speed at block 260 and changes in grade at block 270 may be calculated for each of the plurality of test time increments (e.g., such as dividing a total test time into 10, 20, 25, 30, 35, 40, 50, 75, or 100 etc. time increments and calculating changes in speed and grade in accordance with descriptions above with respect to blocks 260 and block 270).

The changes in work rate and speed range calculated then may be spread over the total test time. For instance, the work rate to speed range can be spread over 21 increments of time (e.g., periods), where the first increment is maintained for 3 minutes and the remaining 20 increments each last for 30 seconds to result in a duration of 10 minutes. In another example, 15 second periods of time may be achieved by taking a total of 41 increments, the first of which would be maintained for 3 minutes and the remaining 40 increments executed with 15 second periods of time. Further, according to embodiments, a more minimal or minimum increment duration (e.g., such as for increments having periods of duration of 1, 2, 3, 5, or 10 seconds) can be achieved and calculated by considering the mechanical properties of the treadmill in terms of resolution in adjustment of grade and speed such that the small increments in grade and speed are minimized according to the physical properties of the treadmill. Thus, a more 'truly continuous' ramp profile change in work rate may be achieved (e.g., more smooth or continuous than the function equation (j) offers for 30 second increments).

For example, in accordance with embodiments, a treadmill increase in speed and grade may be calculated according to the equation:

$$\text{grade}(t) \sim \{[(WR_{max}/m \cdot g \cdot V_0) - \text{grade}_0] \cdot (t) + x \cdot \text{grade}_0\}/\{[(V_{max}/V_0)-1] \cdot (t) + x\} \quad (k)$$

wherein 'x' is an integer between 6 and 25 (e.g., such as a total test time duration or a test duration in minutes as described herein), and it is an integer that increases in a range from 1 to 'x' and is proportional to a number of minutes or amount of time of a treadmill test, $WR_{max}$ is the predicted peak work rate, 'm' is a body mass in kg for the test subject, 'g' is gravitational acceleration (9.81 m/sec$^2$), $V_0$ is the initial treadmill speed, $V_{max}$ is the maximum treadmill speed, and $\text{grade}_0$ is the initial angle of inclination.

The initial grade may then be selected such as is described above at block 270. For example, in embodiments, the initial grade test time could be low, but greater than '0', such as 1 percent. The inclination for each of the remainder of the test time is then calculated such as is described above at block 270. Thus, according to embodiments, the angle of inclination over time for a test treadmill may be calculated prior to the test, such as according to equation (j) or (k) as described herein and corresponding to simultaneous changes in speed as described above with respect to block 260.

For instance, the change in treadmill angle of inclination may be a direct physical change in the treadmill position, such as caused by lifting the front of the treadmill upwards (e.g., such as by raising the position of roller 122 via support 112) such that the test subject walking on the treadmill is walking more upwards. Work is defined as m·g·h (where 'm' is the body mass, 'g' is the gravitational acceleration and 'h' is the vertical displacement). In practice, work occurs on the treadmill with each "step" the test subject takes, such as when the point of initial contact of a step and the point of removal of contact for that step define a difference in height oriented parallel to the vector of 'g' (e.g., such as vector 165). Thus when the angle of inclination is increased, the test subject does greater physical work even at the same speed. Hence, correspondingly, an increase in the treadmill angle of inclination causes an increase in the height of the location to which the test subject's center of gravity must be moved with each step.

Furthermore, in embodiments block 260 and block 270 may be performed in an order opposite that shown in FIG. 2, and/or may be performed during a test, (such as by incorporating blocks 260 and 270 into block 280 and calculating changes in speed and grade in "real time" during testing of the test subject). Also, according to embodiments, block 240 and block 250 may be performed in a reverse order of that shown in FIG. 2, and/or may be performed prior to block 220 and/or prior to block 210.

Next, at block 280 a test subject is tested according to a protocol as determined by blocks 210 through 270. Specifically for example, the initial grade and speed, and calculated changes in grade and speed may be applied during a treadmill test of the test subject until the test subject is exhausted (e.g., such as physically exhausted to the point where the test subject cannot continue exercising on the treadmill even though encouraged to do so). Moreover, according to embodiments, the oxygen consumed by the text subjects, as well as other metabolic and/or physiological responses may be measured, and/or recorded at block 230.

At decision block 282 it is determined whether the test subject is exhausted before the selected total test time (e.g., such as described above with respect to block 210). If the test subject is exhausted before the selected total test time, at block 290 the magnitude and pattern of the oxygen consumed by the test subject during the test is recorded. Note that according to embodiments the treadmill protocols describe herein may also be useful in tests in which oxygen consumption is not measured.

On the other hand, if at block 282 the test subject is not exhausted before the selected total test time, changes in speed and grade for an extended time may be provided. For example, changes in speed and grade for an extended time beyond a total test time (e.g., such as for a test extended time period as described above with respect to FIG. 1 and/or block 210) may be calculated such as described above with respect to blocks 260 and 270.

In accordance with embodiments, changes in speed and grade for an extended time beyond a total test time may have been calculated prior to block 280 (e.g., such as by calculating changes in speed and grade for an extended time at blocks 260 and 270 prior to testing the test subject). Also, in embodiments, it is possible to consider the current speed and grade at the end of the total test time as initial grade and initial speed for calculating changes in speed and grade for the extended time). Additionally, the changes in speed and grade for the extended time may be calculated for a plurality of test time increments of extended time, similar to calculations or test time increments as described above with respect to blocks 260 and 270. Moreover, changes in speed and grade for an extended time may be extrapolated from the calculations provided at blocks 260 and 270 as described above.

After block 284, the process of FIG. 2 returns to block 280 where the testing of the test subject may be continued for the extended time (e.g., for a maximum total test duration time greater than the selected total test time described above with respect to block 210), such as until the test subject is exhausted.

Although the previous discussion was with regard to determining a change in treadmill speed and angle of inclination with respect to time, the same principals can be applied to calculating a change in speed and angle of inclination of exercise equipment with moving stairs or steps. For example, analogously, with regard to stair or "stepper" exercise equipment; stair speed control data may be used to cause a change over time in the speed at which the stairs or steps are being traveled up by the test subject, and angle of inclination control data can cause a change in the angle of the axis running through the stairs in the direction they are traveling (e.g., such as an access running through the center point of each stair's platform) corresponding to changes in treadmill angle of inclination described herein. Also, changes in treadmill angle of inclination over time described herein can be applied to change the height between successive stairs, such as by increasing the height between successive stairs corresponding to an increase in the height that occurs with each "step" of the test subject on the stairs. Thus, increasing the speed of the treadmill belt, the angle of inclination of the treadmill belt, the speed at which stairs are being traveled, and/or the height between each stair being traveled will cause the test subject to do more work per unit time since the test subject will be required to lift the test subject's body weight more frequently and or higher within that same period of time.

For example, at the zero limit of height or angle of inclination (e.g., where 'h' equals zero) the stairs being traveled by the test subject become a flat belt or ramp similar to the belt of a treadmill having a zero angle of inclination (e.g., thus a test subject may walk the zero height stairs or zero angle of inclination treadmill surface at a standard walking speed, or theoretically at any other speed, without performing any "net work").

Subjects and Experiment Design

In one application, according to an embodiment, sedentary healthy subjects (9 female and 13 male) age range 18 to 54 years (mean: 37.6±12.3 years), each performed the treadmill protocol on a Type 2000, SensorMedics, treadmill having a speed continuously adjustable from 0.0 to 13.5 miles per hour and a continuously adjustable grade from 0.0 to 25.0 percent. The protocol included three minutes at the initial velocity and grade followed by the incremental phase as described above. The subjects were not allowed to grasp the handrails or employ any other form of partial support during the test. Subjects were divided into two subgroups. In order to facilitate testing of the linearity of the responses, in 8 out of 22 subjects (sample of convenience) the work rate slopes of the cycle and treadmill tests were chosen to be identical (15 Watts/min) and the test was stopped at 150 Watts in each case. The remaining 14 subjects performed ramp exercise tests to the limit of tolerance. The subjects were verbally encouraged to continue exercise for as long as possible. In these subjects, the treadmill protocol was designed as indicated above. The slope of the work rate increase was altered (e.g., 10, 15 or 20 Watts/min), depending on the subject's estimated exercise tolerance. These tests allowed determination of differences in the overall pattern of response as well as peak exercise responses.

Measurements

During the protocol pulmonary minute ventilation ($V_E$) and gas exchange (oxygen uptake ($VO_2$) and carbon dioxide output ($VCO_2$)) were determined breath by breath with a commercial metabolic measurement system (Vmax 229™ commercially available from SensorMedics of Yorba Linda, Calif., USA). The system was calibrated for airflow and gas concentrations before each test and the system accuracy was checked periodically using a metabolic simulator 19. The 12-lead electrocardiogram was recorded electronically (Corina, Cardiosoft, SensorMedics, Yorba Linda, Calif., USA) and the heart rate was derived from the R-R interval (e.g., the interval in seconds, between the beats or the R wave peaks of adjacent normal cardiac rhythm or QRS complexes). The breath-by-breath data were interpolated to one-second intervals and the averages of uniform 10 sec bins were used for graphical purposes and further calculations.

Statistical Analysis

Sigma Plot 2000 (SPSS Science, Chicago, Ill.) was used for graphical display and calculating basic statistics (mean, SD) and linear regression analysis; Microsoft Excel 2000 was used for conducting paired t-tests. Differences were deemed to be significant at P<0.05.

Results

Figure 3A:
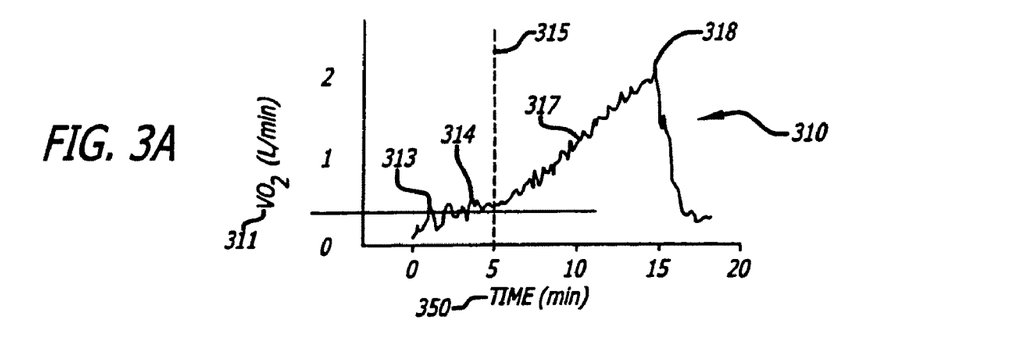
FIG. 3A is a graph showing the rate of oxygen consumption by a test subject for a single test subject, tested on a treadmill, according to one embodiment of a treadmill test protocol.
Figure 3B:
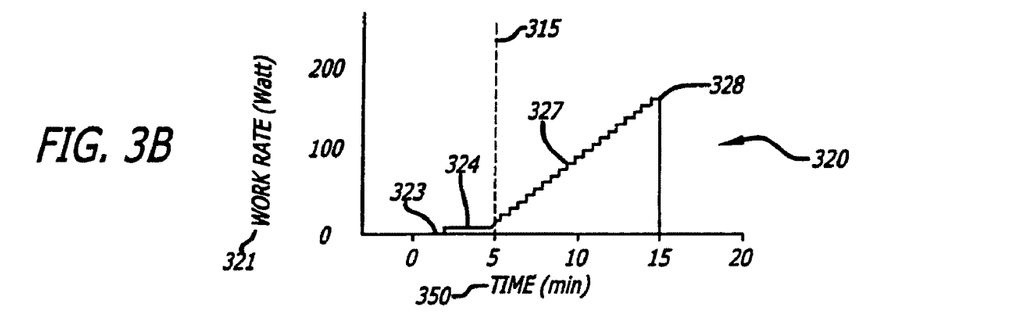
FIG. 3B is a graph showing the work rate of a test subject, tested on a treadmill, according to one embodiment of a treadmill test protocol.

FIG. 3A is a graph showing the rate of oxygen consumption by a test subject, tested on a treadmill according to one embodiment of a treadmill test protocol. Moreover, FIGS. 3A and 3B show a linear increases in both calculated work rate and in the consequent oxygen uptake response during an exercise test that lasted approximately 10 minutes for a representative subject who performed maximal tests, according to one embodiment, incorporating a linear increase in walking speed with a treadmill grade that increases curvilinearly. The walking speed for this test protocol began at 0.7 meters per hour (mph) and a grade of 2.7 percent producing an initial control-phase $VO_2$ of less than 0.5 L/min. Following this initial period, the walking speed and grade for the test protocol were then increased according to equation (j), and as shown and described below for speed graph 340 and inclination graph 330 of FIGS. 3C and 3D.

Figure 3C:
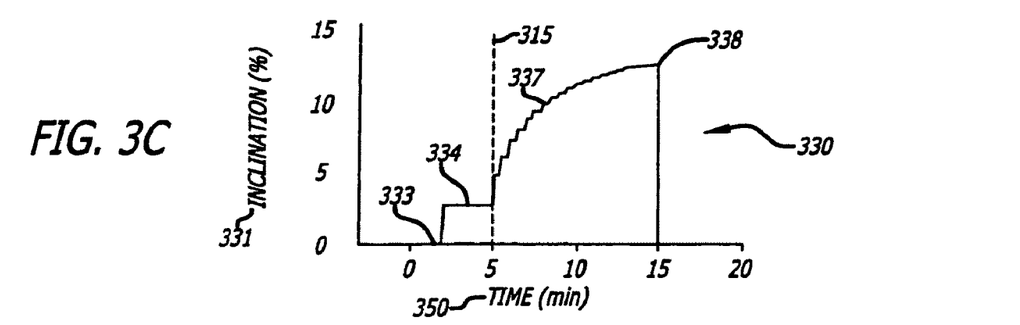
FIG. 3C is a graph showing the inclination of a test subject, tested on a treadmill, according to one embodiment of a treadmill test protocol.
Figure 3D:
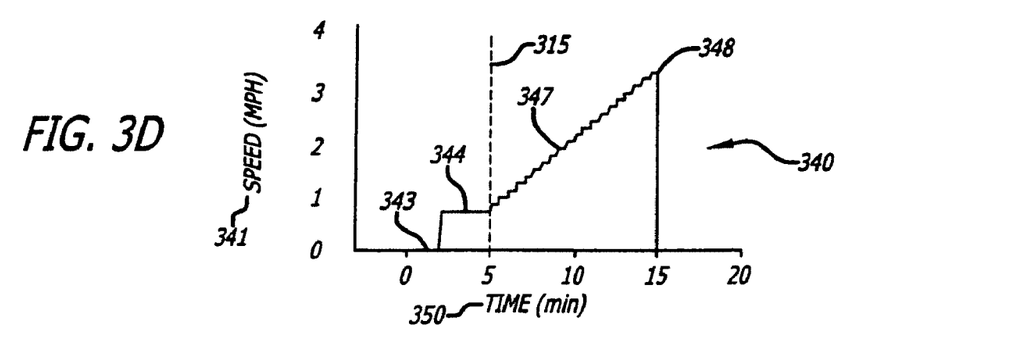
FIG. 3D is a graph showing the speed of a test subject, tested on a treadmill, according to one embodiment of a treadmill test protocol.

Specifically, FIG. 3D is a graph showing the speed of a test subject, tested on a treadmill, according to one embodiment of a treadmill test protocol. Speed graph 340 shows changes in treadmill speed 341 from pretest speed 343 (0.7 mph) to test initialization speed 344, to approximately linear increase in treadmill speed 347 to maximum treadmill speed 348 over time 350 (e.g., such as over time as described above with respect to block 210, and/or a plurality of test time increments as described above with respect to blocks 260 and 270). For example, in accordance with embodiments, pretest conditions may describe conditions of a treadmill and test subject prior to test initialization, such as for a period prior to when the test subject steps on to the treadmill. Similarly, test initialization conditions may describe the condition of a treadmill and test subject during a "warm up", such as a three-minute warm up prior to increasing treadmill speed and/or angle of inclination. More particularly, test initialization time 315 may define a time where the initial test speed 344 may be increased with respect to time (e.g., such as described with respect to block 260 and/or test protocols described herein) until increase in treadmill speed 347 reaches maximum treadmill speed 348. In addition in accordance with embodiments, initialization speed 344 may be similar to initial speed as described with respect to block 250 above, increase in treadmill speed 347 may be similar to calculated changes in speed as described above with respect to block 260, and maximum treadmill speed 348 may be similar to maximum treadmill speed as described above with respect to block 250. According to embodiments, maximum treadmill speed 348 may be a suitable speed such as a speed in the range of between one and 20 miles per hour (mph) (e.g., specifically, such as approximately 2.5 mph, 2.75 mph, 3 mph, 3.1 mph, 3.2 mph, 3.3 mph, 3.5 mph, or 3.75 mph). It should be noted, however that the linearity of measured oxygen uptake and calculated work rate deviates from the already established linear slope above speeds that require the test subject to jog or run other than walk. This speed range may be avoided (and in fact may be excluded) in order to utilize the advantage of the described treadmill protocol in its full extent. This deviation of oxygen uptake vs. work rate slope usually occurs above speeds of about 4.0 mph.

Similarly, FIG. 3C is a graph showing the inclination of a test subject, tested on a treadmill, according to one embodiment of a treadmill test protocol. Angle of inclination graph 330 shows changes in angle of inclination 331 from pretest angle of inclination 333, test initialization angle of inclination 334, and non-linear change in treadmill angle of inclination 337, to maximum angle of inclination 338 overtime 350 (e.g., such overtime is described above with respect to graph 340). Thus, angle with inclination may increase to an angle of inclination potential maximum, such as an angle of inclination corresponding to a inclination percentage where the maximum angle of inclination approximates 90° and corresponds to inclination percentage of 100 percent. For example, according to embodiments, treadmill angle of inclination 337 may change with respect to time inversely proportional to an increase in treadmill speed with respect to time. More particularly, according to embodiments, the change in treadmill angle of inclination with respect to time may be inversely related to the treadmill speed with respect to time, may be inversely proportional to the treadmill speed with respect to time, and/or the treadmill angle of inclination with respect to time may be inversely proportional to a product of the treadmill speed with respect to time and time (e.g., where time is measured in seconds, and/or minutes). Furthermore, according to embodiments, the change in treadmill angle of inclination may approximately model a non-linear, an inverse tangential, a parabolic, an elliptical, and a sinusoidal increase in angle of inclination with respect to time.

Also, according to embodiments, the treadmill angle of inclination over time may decrease at a rate that is inversely proportional to the treadmill speed over time, and/or may approach a maximum angle of inclination limit over time (e.g., such as a maximum angle of inclination defined by maximum angle of inclination 338). For instance, a rate of increase of the treadmill angle of inclination during a period of time, such as 10 minutes, may be decreased, such as by decreasing the rate if increase at a rate that is inversely proportional to the treadmill speed over time. Moreover, according to embodiments, the treadmill angle of inclination over time may be inversely proportional to a product of the treadmill speed with respect to time and time.

According to embodiments, maximum angle of inclination 338 (e.g., whether angle 338 is a maximum approachable angle or the angle of inclination at the termination of the task, such as at the point when the test subject is exhausted) may be a suitable inclination percent such as a percent in the range of between 3% and 25% (e.g., specifically such as 5%, 9%, 10%, 12%, 15%).

According to embodiments determining treadmill test control data, such as treadmill speed control data and/or treadmill angle of inclination control data may include determining a treadmill test work rate that increases approximately linearly with respect to time (e.g., such as over the test duration and/or total test time as described above with respect to block 210). For example, during calculation described above with respect to blocks 250, and/or 260, and approximately linearly increasing work rate may be calculated equal to the body mass of the test subject in kilograms multiplied by the gravitational acceleration (e.g., 9.81 m/sec$^2$) multiplied by sin(a), where "a" is the angle of inclination.

Specifically, work rate graph 320 of FIG. 3B shows changes in work rate 321 starting with pretest work rate 323, going to test initialization work rate 324, then to approximately linearly increasing work rate 327, to work rate maximum 328. According to embodiments, maximum work rate 328 may be the predicted peak work rate as described above with respect to block 230. Moreover, in embodiments, work rate 327 may be elected, determined, or calculated, such as is described above with respect to block 230, or other appropriate approximately linearly increasing work rate selections, determinations, or calculations based on maximum work rate 328. More specifically, for example, work rate 327 may be calculated based upon equation (a) as described above. Also, in embodiments, work rate 321 and/or 327 as well as corresponding speed 341 and/or speed 347, and/or corresponding inclination 331 and/or inclination 337 may be calculated (a) for a protocol terminating prior to work rate 327 reaching maximum work rate 328, (b) for a protocol for work rate 327 reaching approximately to maximum work rate 328, or (c) for a protocol where work rate 327 increases beyond maximum work rate 328.

Moreover, according to embodiments, a protocol may be used, wherein the non-linear treadmill grade increase with respect to time is calculated according to equation (j) above which is:

$$\text{grade}(t) = \{[(WR_{max}/m \cdot g \cdot V_0) - \text{grade}_0] \cdot t + 10 \cdot \text{grade}_0\} / \{[(V_{max}/V_0) - 1] \cdot t + 10\} \quad (j)$$

wherein, 't' is a number of minutes of time of a treadmill test having a total test time of approximately 10 minutes, $WR_{max}$ is the predicted peak work rate, 'm' is a body mass in kg for the test subject, 'g' is gravitational acceleration (9.81 m/sec$^2$), $V_0$ is the initial treadmill speed, $V_{max}$ is the maximum treadmill speed, and $\text{grade}_0$ is the initial angle of inclination or is the initial treadmill grade.

Thus, in the embodiment the change in treadmill angle of inclination (e.g., change in angle of inclination 337) may be inversely proportional over time to the quotient of the maximum treadmill speed divided by the initial treadmill speed (e.g., inversely proportional over time to $V_{max}/V_0$), and/or may be proportional over time to a test subject's predicted peak work rate (e.g., such as described above with respect to block 230) divided by the product of a test subject's weight and an initial treadmill speed (e.g., such as divided by $m \cdot g \cdot V_0$).

Likewise, as described above (e.g., such as with respect to block 290) embodiments include measuring, and/or recording the oxygen consumed by a test subject during a test (e.g., such as a test as described above with respect to block 280). For example, oxygen consumed graph 310 of FIG. 3A shows changes in rate of oxygen consumption 311 (L/min) from pretest rate 313, to test initialization rate 314, through test rate 317 to rate maximum 318 (e.g., such as the rate of oxygen consumed at the point where the test subject becomes exhausted). Note that according to embodiments, oxygen consumed 311 may correspond to measured and/or recorded oxygen as described above with respect to block 290. Furthermore, in accordance with embodiments, graphs 340, 330, 320, and 310 may coincide with determinations, calculations, selections, and/or measurements over a plurality of test time increments such as described above with respect to blocks 260 and 270.

Figure 4A:
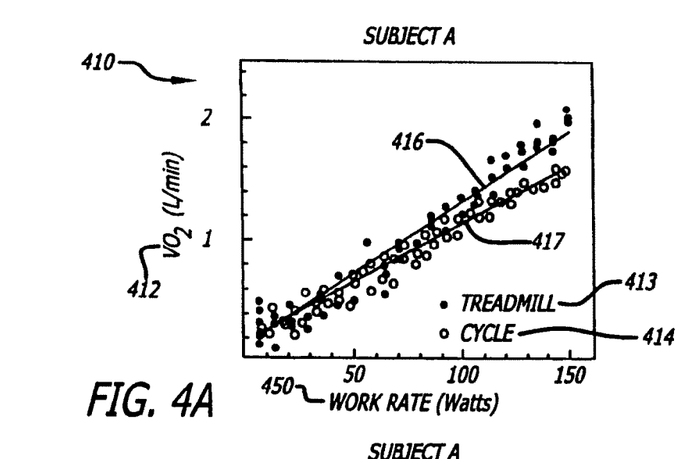
FIG. 4A is a graph of rate of oxygen consumption by test subject A for treadmill tests according to a protocol as compared to rate of oxygen consumption by the same test subject during a cycle test.
Figure 4B:
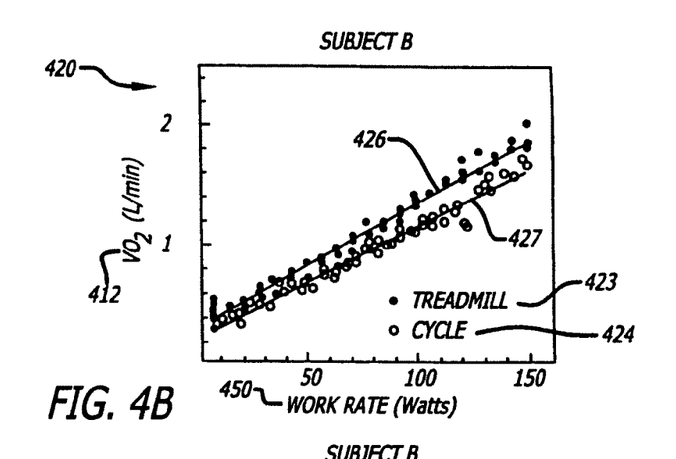
FIG. 4B is a graph of rate of oxygen consumption by test subject B for treadmill tests according to a protocol as compared to rate of oxygen consumption by the same test subject during a cycle test.
Figure 4C:
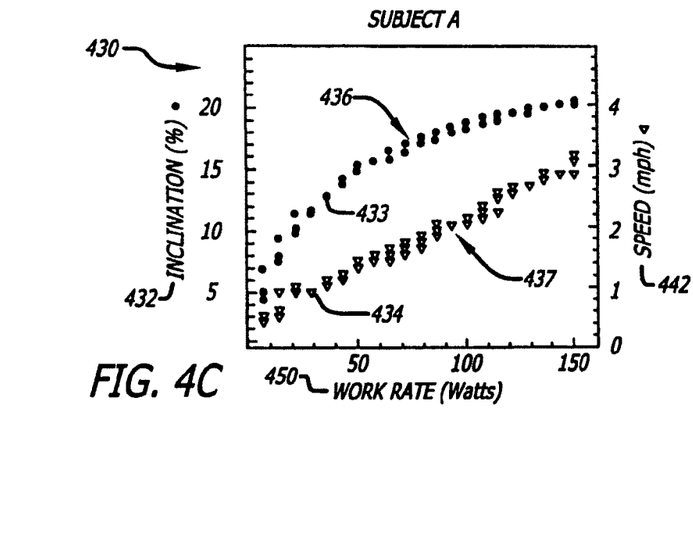
FIG. 4C is a graph of angle of inclination and speed of the treadmill tests of test subject A, according to one embodiment of a treadmill test protocol.
Figure 4D:
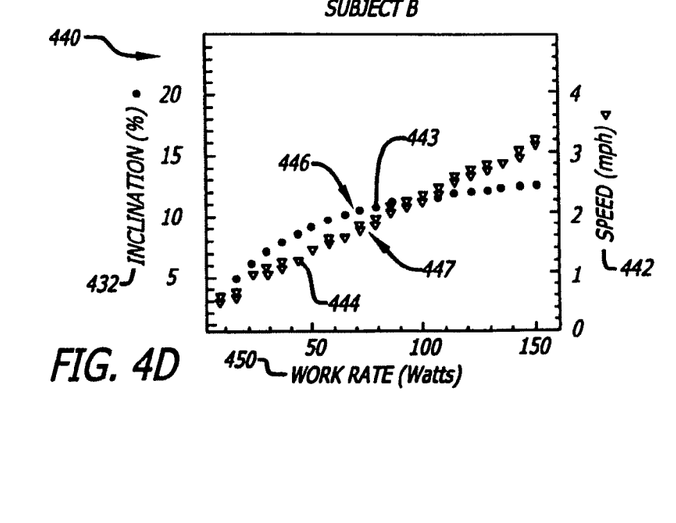
FIG. 4D is a graph of angle of inclination and speed of the treadmill tests of test subject B, according to one embodiment of a treadmill test protocol.

FIG. 4A is a graph of rate of oxygen consumption by test subject A for treadmill tests according to a protocol as compared to rate of oxygen consumption by the same test subject during a cycle test. Moreover, FIGS. 4A and 4B presents the responses of two representative subjects who performed incremental exercise to 150 watts on both a treadmill according to the above equation (j) embodiment of the protocol, and a cycle ergometer. Thus, FIGS. 4A and 4B show a comparison of VO$_2$-Work Rate relationships during ramp tests on the treadmill and on the cycle ergometer, and FIGS. 4C and 4D show the corresponding treadmill speed and inclination settings for subject A and subject B. Subject A: Weight=52 kg, regression parameters; treadmill: c=0.127 L/min, m=12 ml/min/Watt, R2=0.959; bike: c=0.156 L/min, m=9.6 ml/min/Watt, R2=0.967. Subject B: Weight=90 kg, regression parameters; treadmill: c=0.311 L/min, m=10 ml/min/Watt, R2=0.981; cycle: c=0.222 L/min, m=9.1 ml/min/Watt, R2=0.974.

As shown in FIG. 4A, rate of oxygen consumption graph for subject A-410 shows VO$_2$ (L/min) response 412 over work rate (Watts) 450, having treadmill data points 413 with treadmill data point shape 416, as well as cycle data points 414 with cycle data point shape 417. Next, FIG. 4C is a graph of angle of inclination and speed of the treadmill tests of test subject A, according to one embodiment of a treadmill test protocol. Thus, FIG. 4C shows inclination and speed graph for subject A-430 showing inclination (%) 432 and speed (mph) 442 over work rate (Watts) 450. Graph 430 also shows inclination data points 433 having inclination data points shape 436, and speed data points 434 having speed data points shape 437.

Similarly, FIG. 4B is a graph of rate of oxygen consumption by test subject B for treadmill tests according to a protocol as compared to rate of oxygen consumption by the same test subject during a cycle test. Hence, FIG. 4B shows rate of oxygen consumption graph for subject B-420 showing VO$_2$ (L/min) response 412 over work rate (Watts) 450, having treadmill data points 423 with treadmill data point shape 426, as well as cycle data points 424 with cycle data point shape 427. Finally, FIG. 4D is a graph of angle of inclination and speed of the treadmill tests of test subject B, according to one embodiment of a treadmill test protocol. Thus, FIG. 4D shows inclination and speed graph for subject B-440 showing inclination (%) 432 and speed (mph) 442 over work rate (Watts) 450. Graph 440 also shows inclination data points 443 having inclination data points shape 446, and speed data points 444 having speed data points shape 447.

Thus, for lighter test subject A, a similar VO$_2$ response as that for heavier test subject B can be obtained by a protocol similar to those described herein, such as one that calculates subject A inclination data points to have a shape similar to data points shape 436, which has a greater overall magnitude than that of calculated subject B inclination data points (e.g., such as subject B inclination data points) calculated to have the shape similar to data points shape 446. More particularly, note that maximum inclination for subject A is approximately 20% inclination, while maximum inclination for subject B is approximately 10% inclination; and that speed data points shape 437 and speed data points shape 447 are approximately similar. Thus, FIGS. 4A-4D also demonstrates a utilitarian feature according to one embodiment of the proposed treadmill test: the range of both work rate and oxygen uptake measured during the test were effectively the same in two subjects differing considerably in body weights for identical treadmill velocity ranges because the inclination profiles were considerably different. As shown, in the lighter subject, the grade increased to approximately 20 percent whereas in the heavier subject the inclination increased only up to approximately 10 percent.

Note that, while the VO$_2$ response 412 during the treadmill test was a linear function of work rate 450, the slope of the VO$_2$-work rate relationship (e.g., shapes 416 and 426) was higher than that for the same subject's corresponding VO$_2$ response achieved on cycle ergometer (e.g., shapes 417 and 427).

Figure 5A:
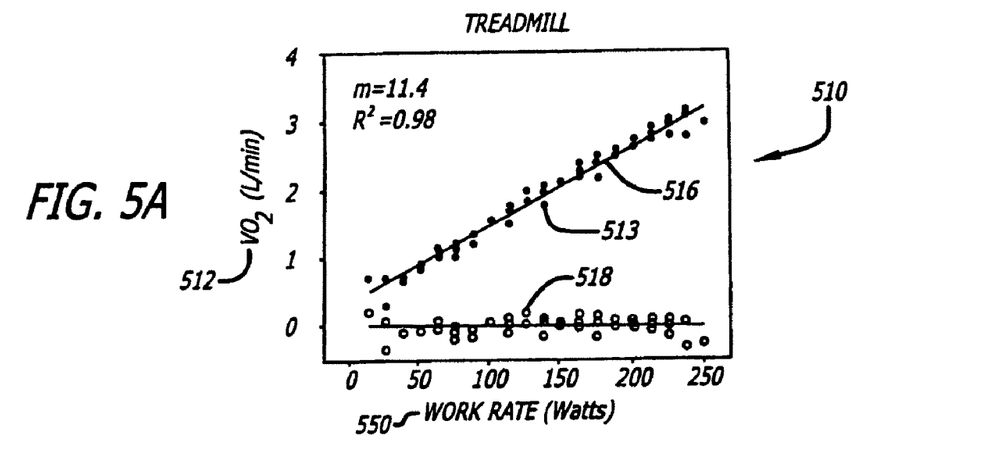
FIG. 5A is a graph of rate of oxygen consumption by a high exercise tolerance test subject obtained utilizing a treadmill test protocol.

Likewise, FIG. 5A shows graphs of rate of oxygen consumption by a high exercise tolerance test subject obtained utilizing a treadmill test protocol. Specifically, FIG. 5A shows the linearity of VO$_2$/work rate slope during ramp tests on the treadmill via subject with high exercise tolerance graph 510, plotting rate of oxygen 512 with respect to work rate 550, having data points 513, and having residuals 518, wherein the residuals are to scale 540 and represent the difference between actual data points 513 and linear regression model 516 (e.g., such as a linear model fit for the data points).

Figure 5B:
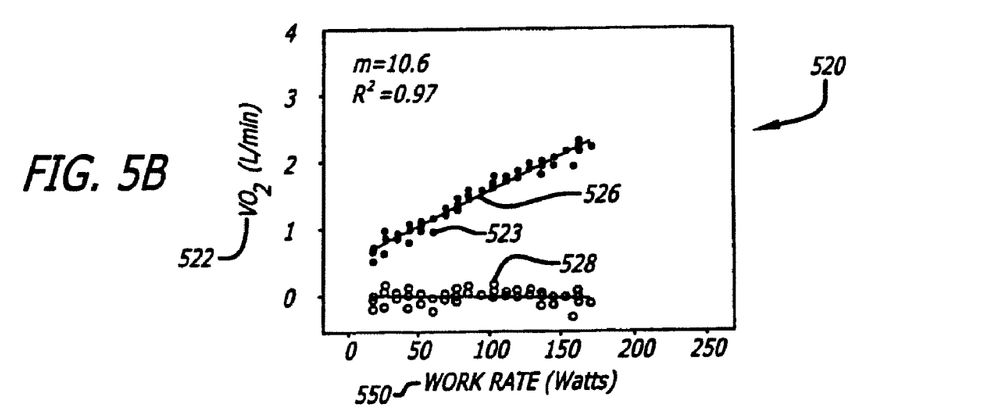
FIG. 5B is a graph of rate of oxygen consumption by a low exercise tolerance test subject obtained utilizing a treadmill test protocol.

Similarly, FIG. 5B is a graph of rate of oxygen consumption by a low exercise tolerance test subject obtained utilizing a treadmill test protocol. Thus, FIG. 5B has subject with low exercise tolerance graph 520 showing rate of oxygen consumption 522 with respect to work rate 550, having data points such as data point 523, and residuals such as residual 528, wherein residuals 528 are to scale 540 and represent the difference between linear regression model 526 and actual data points 523. Note that in graph 520, data points 523 do not progress as far up the axis of work rate 550 or the axis of rate of oxygen 522 as do data points 513.

Figure 5C:
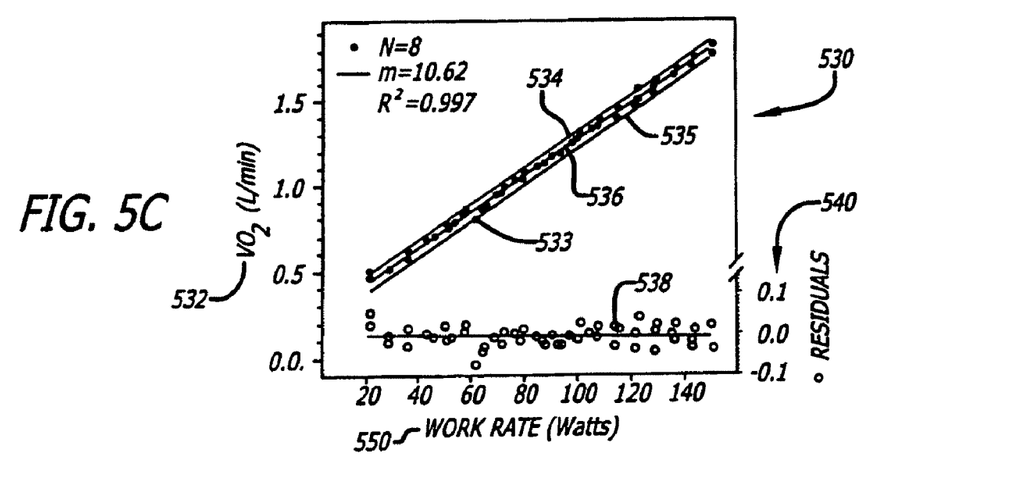
FIG. 5C is a graph of rate of oxygen consumption by an average of eight test subjects obtained utilizing a treadmill test protocol.

Consequently, FIG. 5C is a graph of rate of oxygen consumption by an average of eight test subjects obtained utilizing a treadmill test protocol. Hence, FIG. 5C has ensemble-average data graph 530 showing results for 8 subjects in which the incremental test was done on the treadmill at 15 Watts/min and the incremental test was stopped at 150 W. More particularly, graph 530 shows rate of oxygen consumption 532 with respect to work rate 550, having data points 533 and residuals 538, wherein residuals 538 are to scale 540 and represent the difference between actual data points 533 and linear regression model 536. Moreover, graph 530 shows upper 95% prediction interval 534, and lower 95% prediction interval 535.

Also note that graph 530 shows residuals scale 540 which is applicable to residual 518 and residual 528, as well as residuals 538. Moreover, note that with respect to graphs 510, 520, and 530 that there is a near linear relationship between work rate and rate of oxygen consumption. Thus, in FIGS. 5A-5C, the very high regression coefficients and the minimal variation of residuals around zero suggest that the response is, in fact, linear.

Hence, according to embodiments, an approach for applying a ramp-wise increase in work rate on the treadmill may be provided by a protocol with a linearly increasing work rate profile achieved by a linear increase in walking speed, starting with slow walking, and a time course of treadmill inclination calculated to provide the linear increase in work rate. Specifically, a non-linear treadmill inclination can be calculated according to an equation suitable to be programmed into contemporary computerized system, so that this treadmill protocol can be implemented under computer control. Therefore, a linear $O_2$ uptake response may be elicited by this protocol from both active and sedentary subjects with a substantially wide range of exercise tolerance. Also, patients with lower exercise tolerances (such as those with cardiovascular and pulmonary disease) would be able to operate over a lower region of the work rate profile for the same projected duration.

While several embodiments are described, those skilled in the art will recognize that the spirit and scope of the claims are not limited to the embodiments described, but can be practiced with modification and alteration. The description is thus to be regarded as illustrative instead of limiting.

What is claimed is:

1. A method comprising:
    generating a plurality of treadmill test control data related to a predicted peak work rate for a test subject of a treadmill test over a total test time prior to beginning the treadmill test, wherein when executed, the plurality of treadmill test data causes:
    a linear change in treadmill work rate with respect to time for the total test time based on:
    a linear change in treadmill speed with respect to time for the total test time, and
    a simultaneous non-linear increase in treadmill angle of inclination with respect to time for the total test time, wherein the change in treadmill angle of inclination with respect to time is dependent upon the linear change in treadmill speed with respect to time.

2. The method of claim 1, wherein the change in treadmill work rate is a linear increase with respect to time, and wherein the change in treadmill speed is a linear increase in treadmill speed with respect to time.

3. The method of claim 1, wherein the change in treadmill angle of inclination asymptotically approaches a maximum angle of inclination limit over time, wherein the change in treadmill speed and the change in treadmill angle of inclination depend on the predicted peak work rate and the total test time.

4. The method of claim 1, wherein the change in treadmill angle of inclination with respect to time is inversely proportional over time to the quotient of a maximum speed for the treadmill test divided by an initial speed for the treadmill test and is proportional over time to the predicted peak work rate divided by a product of a weight of the test subject and the initial speed of the treadmill test.

5. The method of claim 1, further comprising dividing the total test time into a plurality of test time increments, and wherein generating includes calculating for each of the plurality of test time increments (1) a linear increase in treadmill speed with respect to time and (2) a corresponding non-linear increase in treadmill angle of inclination with respect to time.

6. A method comprising:
    generating a plurality of treadmill test control data related to a predicted peak work rate for a test subject of a treadmill test over a total test time prior to beginning the treadmill test, wherein when executed, the plurality of treadmill test data causes:
    a linear change in treadmill work rate with respect to time for the total test time based on:
    a linear change in treadmill speed with respect to time for the total test time, and
    a simultaneous non-linear increase in treadmill angle of inclination with respect to time for the total test time, wherein the change in treadmill angle of inclination with respect to time is dependent upon the linear change in treadmill speed with respect to time,
    wherein the change in treadmill angle of inclination defines a function derived by calculating a treadmill grade curve that changes with respect to time according to $[(WR_{max}/m \cdot g \cdot V_0) - grade_0]$, and $1/[(V_{max}/V_0) - 1]$, wherein, $WR_{max}$ is the predicted peak work rate, 'm' is a body mass for the test subject, 'g' is gravitational acceleration, $V_0$ is an initial treadmill speed for the treadmill test, $V_{max}$ is a desired maximum speed for the treadmill test, and $grade_0$ is an initial angle of inclination for the treadmill test.

7. A method comprising:
    generating a plurality of treadmill test control data related to a predicted peak work rate for a test subject of a treadmill test over a total test time prior to beginning the treadmill test, wherein when executed, the plurality of treadmill test data causes:
    a linear change in treadmill work rate with respect to time for the total test time based on:
    a linear change in treadmill speed with respect to time for the total test time, and a simultaneous non-linear increase in treadmill angle of inclination with respect to time for the total test time, wherein the change in treadmill angle of inclination with respect to time is dependent upon the linear change in treadmill speed with respect to time, wherein the change in treadmill angle of inclination with respect to time is modeled by grade(t), to increase with respect to a number of minutes of duration in time 't' according to:

$$\text{grade}(t) = \{[(WR_{max}/m \cdot g \cdot V_0) - \text{grade}_0] \cdot t + 10 \cdot \text{grade}_0\} / \{[(V_{max}/V_0) - 1] \cdot t + 10\},\text{ and}$$

wherein $WR_{max}$ is the predicted peak work rate, 'm' is a body mass for the test subject, 'g' is gravitational acceleration, $V_0$ is the initial treadmill speed for the treadmill test, $V_{max}$ is the desired maximum treadmill speed for the treadmill test, and $\text{grade}_0$ is the initial angle of inclination for the treadmill test.

8. A method comprising:
inputting a predicted peak work rate for a test subject of a treadmill test and a total test time of the treadmill test, wherein the produced treadmill test includes a linear change in treadmill work rate with respect to time for the total test time based on:
 a predetermined linear increase in treadmill speed with respect to time for the total test time, and
 a predetermined non-linear change in treadmill angle of inclination with respect to time for the total test time;
testing a test subject on a treadmill with the treadmill test according to the test control data; and
terminating the treadmill test upon exhaustion of the subject.

9. The method of claim 8, further comprising:
measuring a rate of oxygen consumption by the test subject during the treadmill test; wherein the rate of oxygen consumption by the test subject during the treadmill test increases approximately linearly.

10. A method comprising:
predicting a plurality of treadmill test control data for a test subject of a treadmill test prior to initiating the treadmill test according to a plurality of treadmill test control data, wherein the plurality of treadmill test control data includes a non-linear treadmill grade increase and a linear increase in treadmill speed with respect to time.

11. The method of claim 10 further comprising determining an initial angle of inclination for the treadmill test, an initial treadmill speed for the treadmill test, a desired total test time for the treadmill test, a desired maximum treadmill speed for the treadmill test, and a desired peak work rate for the test subject.

12. The method of claim 11, wherein predicting a treadmill test protocol includes predicting an increase in treadmill speed that is proportional to the quotient of the desired maximum treadmill speed for the treadmill test minus the initial treadmill speed for the treadmill test and the total desired test time.

13. The method of claim 12, wherein the desired total test time is 10 minutes, and the non-linear treadmill grade, grade(t), increase with respect to a number of minutes of duration in time according to:

$$\text{grade}(t) / = \{[(WR_{max}/m \cdot g \cdot V_0) - \text{grade}_0] \cdot t + 10 \cdot \text{grade}_0\} / \{[(V_{max}/V_0) - 1] \cdot t + 10\}$$

wherein $WR_{max}$ is the predicted peak work rate, 'm' is a body mass for the test subject, 'g' is gravitational acceleration, $V_0$ is the initial treadmill speed for the treadmill test, $V_{max}$ is the desired maximum treadmill speed for the treadmill test, and $\text{grade}_0$ is the initial angle of inclination for the treadmill test.

14. An article of manufacture comprising:
a machine-readable medium having data therein which when accessed by a processor causes the processor to:
 generate a plurality of treadmill test control data related to a predicted peak work rate for a test subject of a treadmill test over a total test time prior to beginning the treadmill test, wherein when executed, the plurality of treadmill test data causes:
 a linear change in treadmill work rate with respect to time for the total test time based on:
  a linear increase in treadmill speed with respect to time, and
  a non-linear increase in treadmill angle of inclination with respect to time that depends upon the linear increase in treadmill speed over time.

15. The article of manufacture of claim 14, further comprising data to cause a processor to divide the total test time into a plurality of minimum test time increments, and calculate for each of the plurality of test time increments (1) the linear increase in treadmill speed with respect to time and (2) the dependent non-linear increase in treadmill angle of inclination with respect to time.

16. The article of manufacture of claim 15, further comprising data to cause a processor to:
generate the plurality of treadmill test control data during the total test time and after the beginning of the treadmill test, based on previously inputted weight, age, gender, desired maximum work rate, desired minimum and maximum walking speeds and considering a treadmill maximum possible inclination and a treadmill minimum steps of increments of inclination.

17. The article of manufacture of claim 14, further comprising data to cause a controller to:
vary a treadmill speed of a treadmill test according to the predetermined linear increase in treadmill speed with respect to time, and
vary a treadmill angle of inclination of a treadmill test according to the predetermined non-linear increase in treadmill angle of inclination with respect to time.

18. A system comprising:
a processor;
a memory coupled to said processor and containing code which when executed:
 generate a plurality of treadmill test control data related to a predicted peak work rate for a test subject of a treadmill test over a total test time prior to beginning the treadmill test, wherein when executed, the plurality of treadmill test data causes:
 a linear change in treadmill work rate with respect to time for the total test time based on:
 a linear increase in treadmill speed with respect to time, and
 a non-linear increase in treadmill angle of inclination with respect to time.

19. The system of claim 18, wherein the non-linear increase in treadmill angle of inclination depends upon the increase in treadmill speed over time.

20. The system of claim 19, further comprising the processor dividing the total test time into a plurality of minimum test time increments, and calculating for each of the plurality of test time increments (1) the linear increase in treadmill speed with respect to time and (2) the dependent non-linear increase in treadmill angle of inclination with respect to time.

21. The system of claim 18, wherein the non-linear increase in treadmill angle of inclination is modeled by grade (t), to increase with respect to a number of minutes of duration in time 't' according to:

$$\text{grade}(t) = \{[(WR_{max}/m \cdot g \cdot V_0) - \text{grade}_0] \cdot t + 10 \cdot \text{grade}_0\} / \{[(V_{max}/V_0) - 1] \cdot t + 10\}$$

wherein $WR_{max}$ is the predicted peak work rate, 'm' is a body mass for the test subject, 'g' is gravitational acceleration, $V_0$ is the initial treadmill speed for the treadmill test, $V_{max}$ is the desired maximum treadmill speed for the treadmill test, and $grade_0$ is the initial angle of inclination for the treadmill test.

* * * * *